(12) United States Patent
Meyer et al.

(10) Patent No.: US 7,171,314 B2
(45) Date of Patent: Jan. 30, 2007

(54) METHODS AND SYSTEMS FOR ANALYZING STRUCTURAL TEST DATA

(75) Inventors: Eric S. Meyer, Chesterfield, MO (US); Scott S. Fields, St. Charles, MO (US); Kenneth L. Knopp, Creve Coeur, MO (US); Jeffrey S. Sermersheim, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 55 days.

(21) Appl. No.: 10/955,813

(22) Filed: Sep. 30, 2004

(65) Prior Publication Data

US 2006/0069521 A1  Mar. 30, 2006

(51) Int. Cl.
*G01L 1/00* (2006.01)

(52) U.S. Cl. ............... 702/42; 702/34; 702/35; 702/181; 702/183; 73/577; 73/783; 73/776; 73/802; 324/209; 324/240

(58) Field of Classification Search ............ 702/42, 702/34–35, 30, 182–183; 324/240, 209; 73/577, 783, 802, 776
See application file for complete search history.

(56) References Cited

U.S. PATENT DOCUMENTS

| 3,387,120 | A | 6/1968 | Funk et al. |
|---|---|---|---|
| 3,979,579 | A | 9/1976 | Kleinpeter |
| 4,336,595 | A | 6/1982 | Adams et al. |
| 4,524,620 | A | 6/1985 | Wright et al. |
| 4,722,062 | A | 1/1988 | Breitkopf et al. |
| 4,764,882 | A | 8/1988 | Braschel et al. |
| 4,875,170 | A | 10/1989 | Sakuri et al. |
| 5,490,195 | A | 2/1996 | Berkley |
| 5,816,530 | A | 10/1998 | Grube |
| 5,847,668 | A | 12/1998 | Morita et al. |
| 6,212,486 | B1 | 4/2001 | Huang et al. |
| 6,657,429 | B1 * | 12/2003 | Goldfine et al. ............ 324/232 |
| 6,874,370 | B1 * | 4/2005 | Vachon ........................ 73/808 |

\* cited by examiner

*Primary Examiner*—John Barlow
*Assistant Examiner*—Hien Vo
(74) *Attorney, Agent, or Firm*—Lee & Hayes, PLLC

(57) ABSTRACT

Systems and methods for analyzing structural test data are disclosed. In one embodiment, a method includes applying a sequence of loads to a test article, receiving raw test data indicative of the applied loads from at least one sensor operatively associated with the test article, receiving predicted test data indicative of the predicted loads on the test article, filtering out invalid test data, cycle counting to pair loads in the test data, performing a first fatigue damage computation based on the raw test data, performing a second fatigue damage computation based on the predicted test data, and comparing the first and second fatigue damage computations. The filtering, cycle counting, and performing of the first and second fatigue damage computations, and the comparison of the first and second fatigue damage computations, may be performed simultaneously using a spreadsheet program.

60 Claims, 6 Drawing Sheets

FIG. 4

METHODS AND SYSTEMS FOR ANALYZING STRUCTURAL TEST DATA

FIELD OF THE INVENTION

This invention relates to structural testing, and, more specifically, to methods and systems for accurately and efficiently analyzing real-time structural test data.

BACKGROUND OF THE INVENTION

Due to the time and expense associated with full-scale structural fatigue testing, test laboratories are typically under pressure to reduce their operating expenses and to produce results more quickly. An increase in the cycling rate of a full-scale fatigue test may lead directly to lower laboratory costs and may provide test results sooner. For example, in the aircraft industry, significant potential savings may be realized in retrofit and fleet repair costs if structural fatigue test results can be provided more quickly.

Cycling rate may be a function of many parameters. One parameter that is particularly critical is the accuracy of the applied test loads. Typically there is a required spectrum severity that must be maintained. As the cycle rate increases, there is a potential for the loads to be applied with less accuracy, reducing (or increasing) the severity of the applied spectrum. A current process to evaluate the tested spectrum severity involves applying a significant portion of the spectrum while recording the load feedback and strain gage output. These data are then evaluated, which may take days or weeks before results are known.

SUMMARY OF THE INVENTION

The present invention is directed to methods and systems for analyzing structural test data. Methods and systems in accordance with the present invention may advantageously reduce the time and expense associated with providing accurate structural fatigue test results.

In one embodiment, a method of analyzing structural test data includes applying a sequence of loads to a test article, and receiving raw test data indicative of the applied loads from at least one sensor operatively associated with the test article. The method further includes receiving predicted test data indicative of a predicted load on the test article, performing a first fatigue damage computation based on the raw test data, and performing a second fatigue damage computation based on the predicted test data. The method also includes comparing the first and second fatigue damage computations. The performing of the first and second fatigue damage computations, and the comparison of the first and second fatigue damage computations, may be performed simultaneously using a spreadsheet program.

BRIEF DESCRIPTION OF THE DRAWINGS

Preferred and alternate embodiments of the present invention are described in detail below with reference to the following drawings.

FIG. 4 is an embodiment of a tested actuator loads screen of the method of FIG. 1;

DETAILED DESCRIPTION

The present invention relates to methods and systems for structural testing. Many specific details of certain embodiments of the invention are set forth in the following description and in FIGS. 1–6 to provide a thorough understanding of such embodiments. One skilled in the art, however, will understand that the present invention may have additional embodiments, or that the present invention may be practiced without several of the details described in the following description.

In general, methods and systems in accordance with the present invention enable test personnel to evaluate the effects of applied test load variances, and to make necessary adjustments, in real-time while conducting a test. Data generated by a test article are collected and then processed using methods and systems in accordance with the invention to assess the spectrum severity. Thus, embodiments of the present invention may advantageously provide substantially real-time analysis results during a test, thereby reducing the time and expense associated with providing accurate structural fatigue test results.

Figure 1:
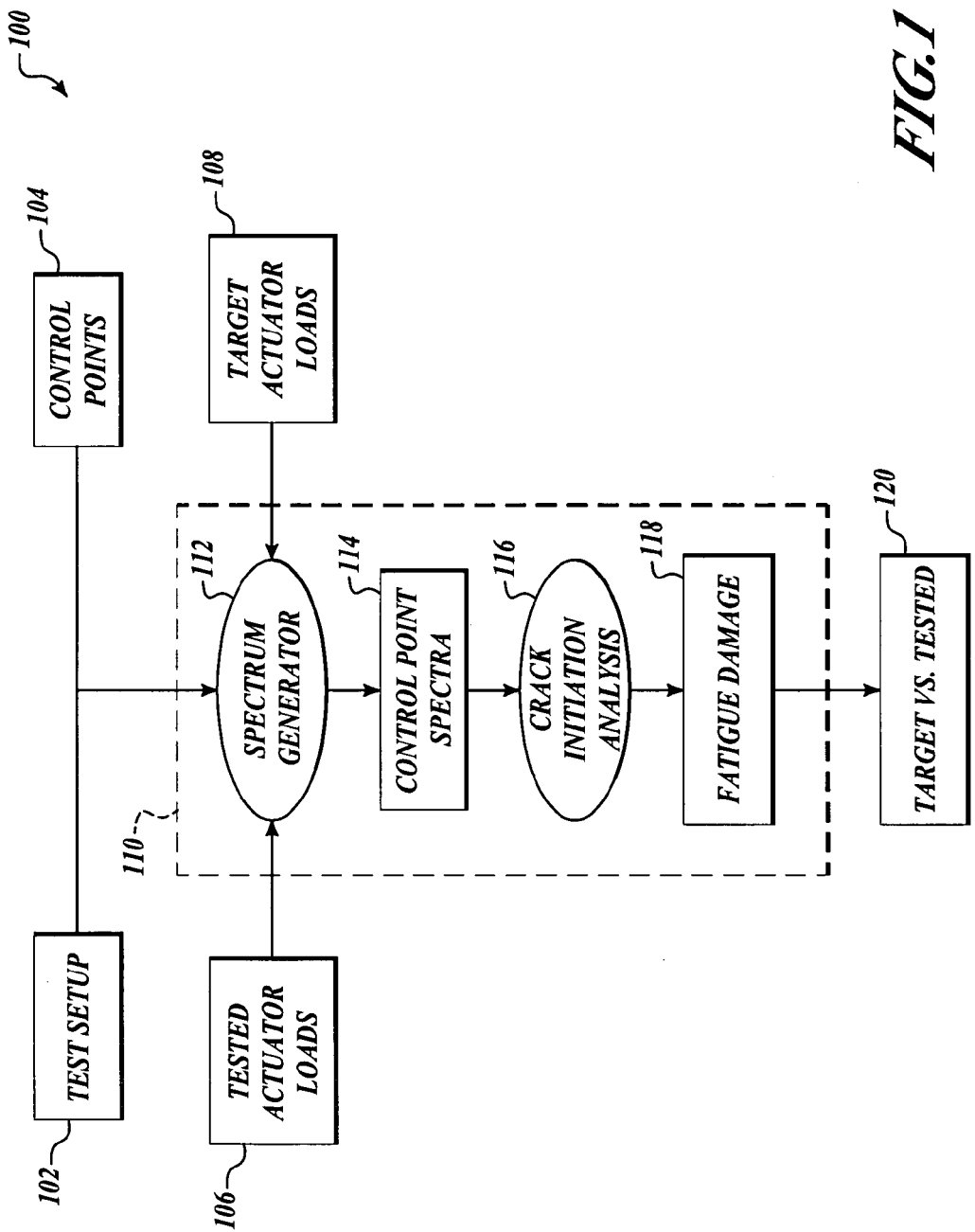
FIG. 1 is a flowchart of a method for performing a structural test in accordance with an embodiment of the invention.
Figure 2:
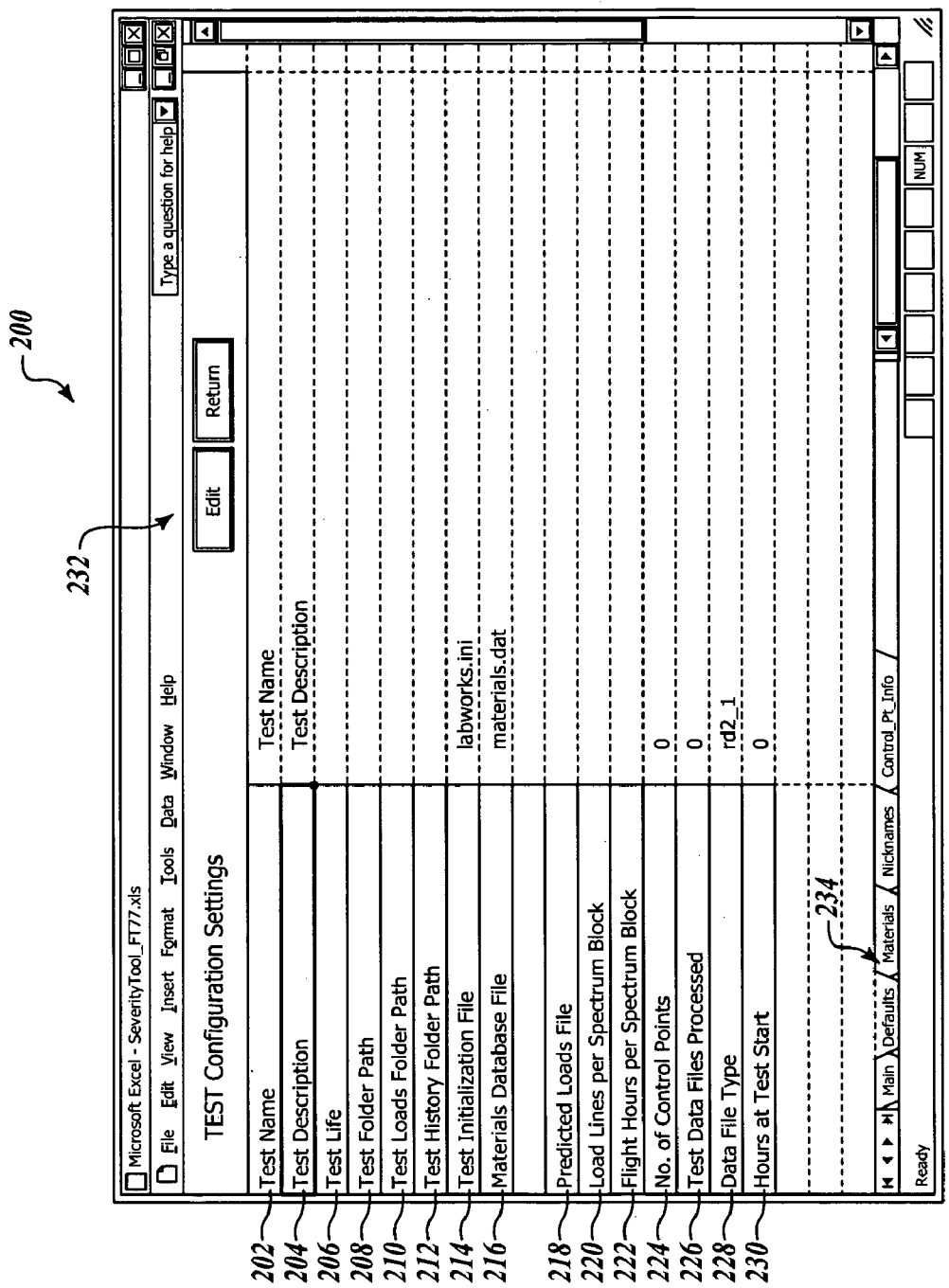
FIG. 2 is an embodiment of a test setup input screen of the method of FIG. 1.

More specifically, FIG. 1 is a flowchart of a method 100 for performing a structural test in accordance with an embodiment of the present invention. In the embodiment, the method 100 begins with a test setup at a block 102. In one embodiment, the test setup (block 102) is performed via a menu or spreadsheet-formatted input screen 200, as shown in FIG. 2. During the test setup, a user may define the following parameters:

Test Name 202—a brief identifier for the test to be conducted;

Test Description 204—a description of the test to be conducted;

Test Life 206—a duration of the subject test (e.g., in flight hours);

Test Folder Path 208—a path name to a folder for storing test data;

Test Loads Folder Path 210—a path name to a folder for storing loads data;

Test History Folder Path 212—a path name to a folder for storing processed test data for subsequent analysis by an analysis engine;

Test Initialization File 214—a filename of an initialization file created by the method 100 that will be supplied to a crack initiation engine (described below);

Test Materials Database File 216—a filename of a file containing a list of materials and the material properties required to perform a crack initiation analysis;

Test Predicted Loads File 218—a filename of a file containing a set of predicted loads for the subject test;

Test Spectrum Load Lines per Block 220—a number of load events that will be repeated as a block throughout the test;

Test Spectrum Flight Hours per Block 222—a number of equivalent flight hours for each block of the test spectrum;

Test Control Points 224—a number of test control points determined by the method 100 (not input by the user), as described more fully below;

Test Data Files Processed 226—a number of test data files processed to date determined by the method 100 (not input by the user);

Test Data File Type 228—an expected format of the resultant test data files; and Flight Hours at Test Start 230—a number of equivalent test flight hours at a start of the test, which is usually "0", but which may be greater then zero to allow for the data processing to start subsequent to the start testing.

The input screen 200 includes navigation buttons 232 that permit a user to edit the inputs described above, and to return to one or more other portions of the method 100. In one particular embodiment, the input screen 200 is a spreadsheet screen generated using the EXCEL program commercially available from the Microsoft Corp. of Redmond, Wash., and includes a plurality of worksheet tabs 234 that enable the user to move swiftly between various portions of the method 100.

Figure 3:
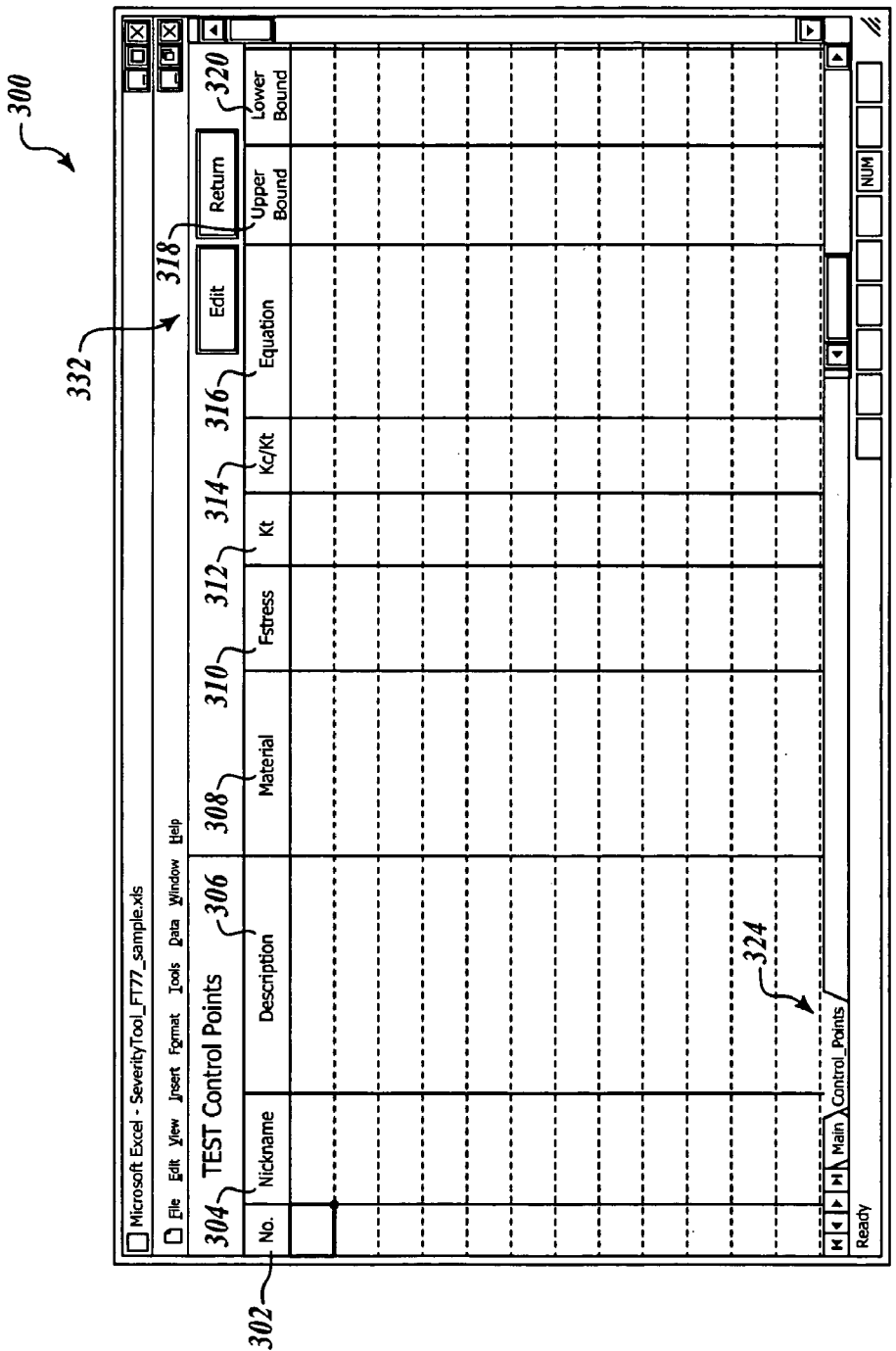
FIG. 3 is an embodiment of a control point input screen of the method of FIG. 1.

As further shown in FIG. 1, the method 100 further includes defining control points at a block 104. The control points are those specific locations on a test article where crack initiation analyses and comparisons will be performed. In one embodiment, the control point definition (block 104) is performed via a control point input screen 300, as shown in FIG. 3. During the control point definition, the user may define the following parameters:

Control Point No. 302—a numeric identifier (e.g., an integer) for a control point;

Name 304—a text identifier (or nickname) for each control point;

Description 306—a text description (e.g., a detailed description) for each control point;

Material 308—a material definition for the control point;

Fstress 310—a factor used in a control point equation to calculate an analytic fatigue stress from the analytical fatigue load output by Equation 316. This factor is used by a crack initiation engine, as described more fully below;

Kt 312—a stress concentration factor used by the crack initiation engine to calculate fatigue damage for the control point;

Kc/Kt 314—a factor that accounts for the fact that a "compression" load path may be different from a "tension" load path, the factor being required by the crack initiation engine to calculate fatigue damage for the control point;

Equation 316—an equation for determining an analytical fatigue load from a plurality of test measurands; actual test measurand names or "nicknames" may be used as variable inputs. Test measurand names or nicknames (i.e., non-constant entries) may be enclosed in brackets, for example Analytical Fatigue Load=[WRBM]*1.00;

UpperBound 318—an upper bound of the equation 316 used to identify erroneous data in a Test Loads file; and LowerBound 320—a lower bound of the equation 316 used to identify erroneous data in a Test Loads file.

Again, the control point input screen 300 may include navigation buttons 322 that permit a user to edit the inputs described above, and to return to one or more other portions of the method 100, and a plurality of worksheet tabs 324 that enable the user to move swiftly between various portions of the method 100.

Figure 4:
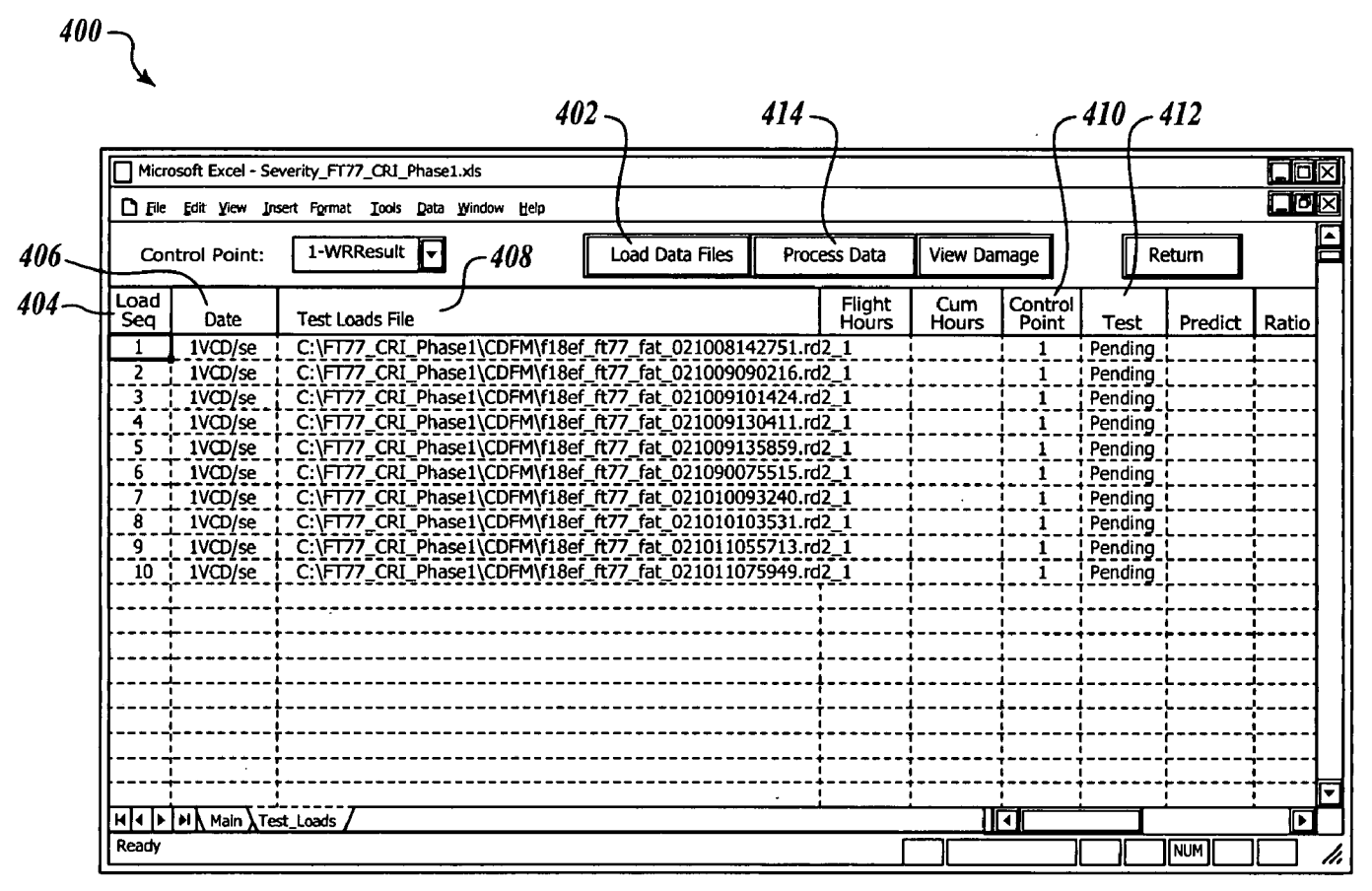

After the test setup is performed (block 102) and the control points are defined (block 104), data processing may start in conjunction with the test. As shown in FIG. 1, the method 100 further includes defining tested actuator loads at a block 106. FIG. 4 is an embodiment of a tested actuator loads screen 400 of the method of FIG. 1. New test data files may be loaded by selecting a load data files command button 402. These test data files may represent the unprocessed test data gathered by the test sensors during applications of loads to the test article. These unprocessed test data may represent raw, unprocessed electrical signal outputs from a variety of different sensors types (e.g., strain gauges, transducers, thermocouples, etc.). When the load data files command button 402 is selected by user, the test loads folder 210 specified in the setup input screen 200 (FIG. 2) will be searched for new test data files. Each selected test data file is assigned a file identifier 404, a date 406, a test loads file name 408, a specified control point 410 for analysis, and a test status 410. Prior to being processed by the method 100, the new files are tagged as having the test status 412 of "pending".

Files loaded and tagged with the "pending" test status 412 may be processed by clicking a process data command button 414. Upon selection of the processed data command button 414, the method 100 may process all of the "pending" files in a background or batch mode. During processing, portions of the tested actuator loads screen 400 may be continuously updated to provide the results of the data processing. Also during the processing, inputs provided by the user during the test setup (block 102) may be employed. For example, at a block 108 (FIG. 1), the method 100 receives target actuator loads contained in the Test Predicted Loads File 218 specified by the user during the test setup (FIG. 2).

Figure 5:
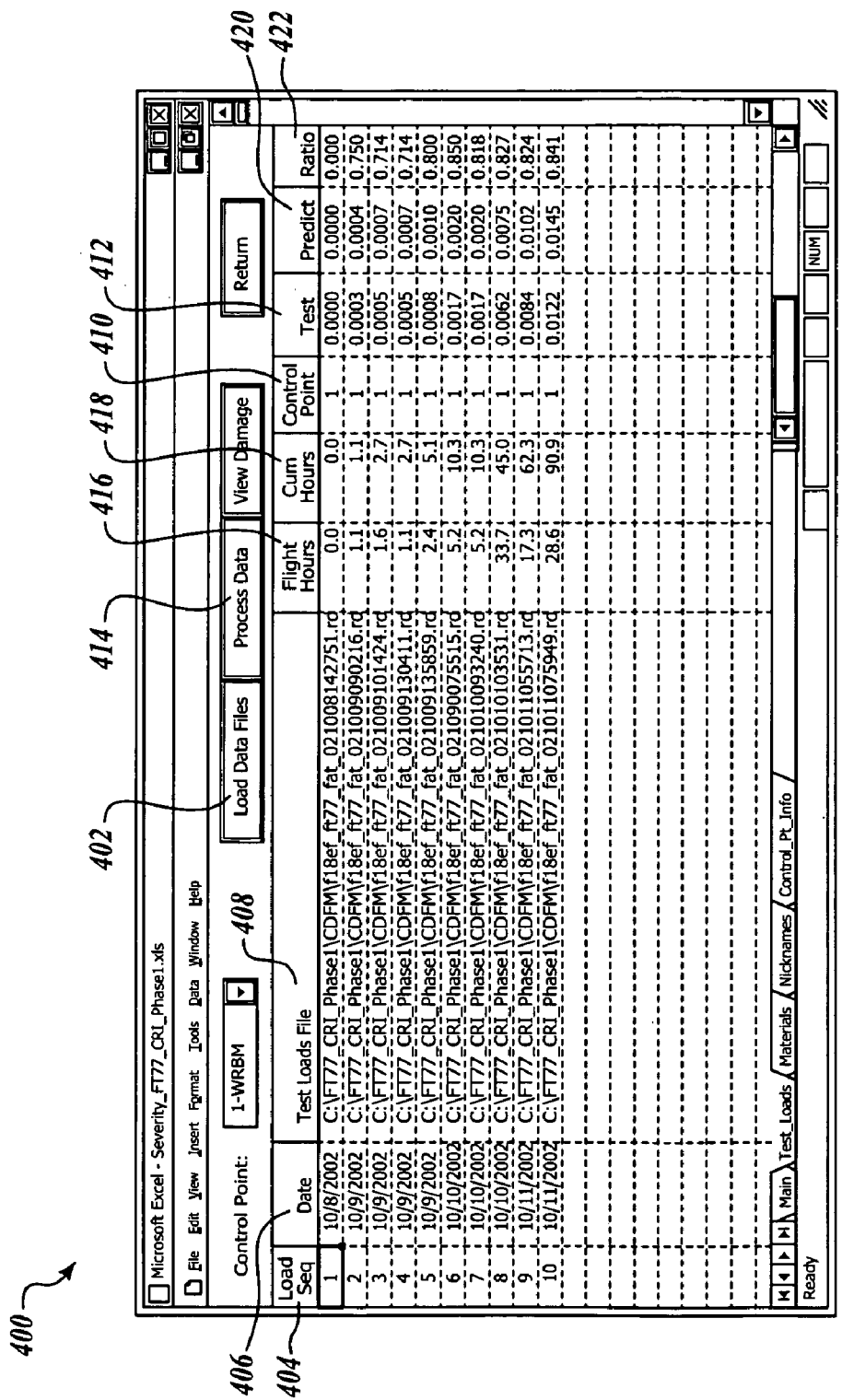
FIG. 5 shows the tested actuator loads screen of FIG. 4 after processing of test data files.

For example, FIG. 5 shows the tested actuator loads screen 400 of FIG. 4 after processing of the test data files 408. As shown in FIG. 5, after the test data files 408 are processed, the tested actuator loads screen 400 provides a flight hours indicator 416 indicating a simulated number of flight hours represented by the test data, a cumulative flight hours indicator 418 indicating a cue at a number of flight hours are presented by the test data (maybe same as the flight hours indicator 416), a predicted test result 420 (e.g., based on analytical predictions, empirical predictions, etc.) for comparison with the actual test results, and an actual test result 422 computed from the raw test data (e.g., transducer outputs, strain gauge outputs, etc.).

The manner in which the actual test results 422 are computed will now be described. Referring again to FIG. 1, the method 100 proceeds to a crack initiation engine at a block 110 to predict crack initiation damage. First, at a block 112, the crack initiation engine (block 110) includes a spectrum generator that performs a cycle counting in which an effective pairing of load peaks and valleys is performed. The spectrum generator filters the sequence of actual test results such that each test point produces a slope change when compared to the previous two test points. Any load points that do not produce a slope change are eliminated from the actual test data. Any load points eliminated from the actual test data are also eliminated from the predicted test data. This filtering process is performed simultaneously for each control point. While filtering, the spectrum generator also identifies invalid actual test results. Invalid results include spikes and dropouts. When the actual test results exceed the bounds 318 and 320 or deviate from the predicted test results by more than 50% and the actual test results are greater than 10% of the upper bound 318, the results are eliminated from both the actual test results and the predicted test results. Actual and predicted test results that are output by the filtering portion of the spectrum generate are immediately used in a cycle counting process which pairs load peaks and valleys. In one particular embodiment, the cycle counting process operates by the generally-known rules of rainflow cycle counting. The cycle counting is performed simultaneously on all control points. When the cycle counting process identifies a paired peak and valley, at a block 114, a control point spectra portion performs a calculation of notch stress and strain based on the applied loads and the elastic KT. In one embodiment, for example, the crack initiation engine 110 implements the nominally elastic Neuber's Equation to determine notch stress and strain. The nominally elastic Neuber's Equation is presented below as Equation (1) in its basic form:

$$K_T^2 = K_\sigma \times K_\epsilon, \quad (1)$$

where:

$K_T$ is the elastic stress concentration factor;

$K_\sigma$ is the plastic stress concentration factor, and $K_\epsilon$ is the plastic strain concentration factor.

Next, a crack initiation analysis is performed at a block 116. In one embodiment, the crack initiation analysis uses an Equivalent Strain Equation, a correction of the calculated notch strain for load cycle stress ratio (R) effects. In one particular embodiment, the crack initiation engine 110 implements the Smith, Watson, and Topper equation to analytically account for mean stress effects. The Smith, Watson, and Topper equation is:

$$\left(\frac{\Delta \varepsilon}{2}\right)_{EQ} = \sqrt{\left(\frac{\Delta \varepsilon}{2}\right)\frac{\sigma_{MAX}}{E}} \quad (2)$$

Where $\frac{\Delta e}{2}$     Applied cycle strain amplitude $\left(\frac{\Delta e}{2}\right)_{EQ}$     Equivalent strain amplitude, after correction for cycle mean strain $E$     Modulus of Elasticity $\sigma_{max}$     Maximum Notch stress for the applied cycle At a block 118, a summation of the calculated damage and the failure criteria is then computed. In one particular embodiment, the crack initiation engine 110 uses the Palmgren and Miner's Rule to sum the damage associated with continued load cycling. Palmgren and Miner's Rule, states:

$$\text{Total Damage} = \sum_{i=1}^{N_T} \left(\frac{1}{N_f}\right)_i \quad (3)$$

In one particular embodiment, crack initiation is assumed to occur when the total damage is equal to 1.0. Crack initiation failure is typically assumed to be the development of a 0.01-inch flaw, although in various embodiments, other crack initiation failure thresholds may be employed.

As shown in FIG. 1, the calculation of fatigue damage (block 118) is performed by the crack initiation engine (block 110) using both the tested actuator loads (block 106) and the target actuator loads (block 108). As shown in FIG. 5, these fatigue damage calculations are output to the user as the actual test data 412 in the predicted test data 420, respectively, for comparison purposes. The ratio 422 (FIG. 5) is the actual test data 412 over the predicted test data 420.

Figure 6:
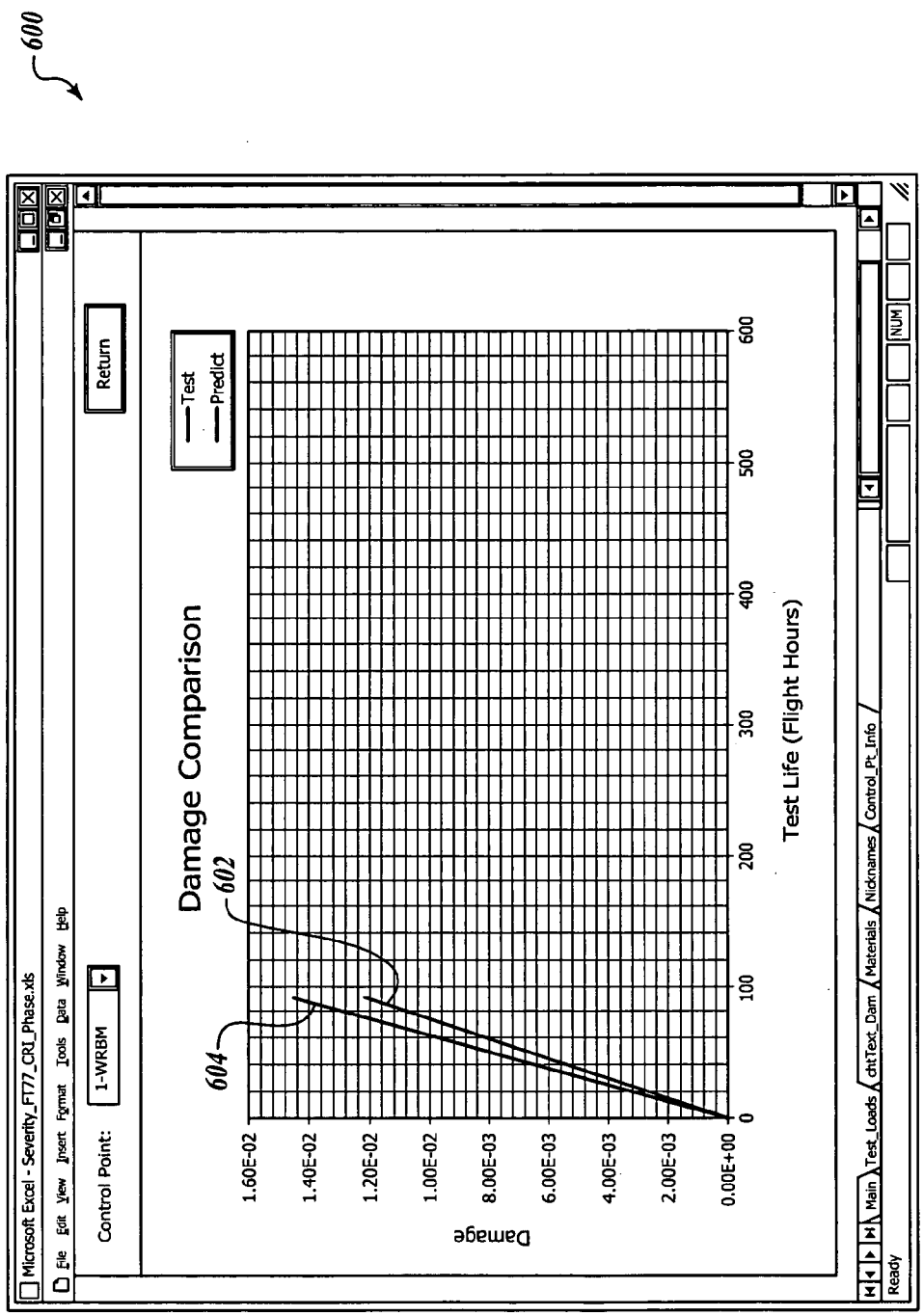
FIG. 6 is a representative plot of damage versus time for comparing the actual and predicted fatigue damages of the method of FIG. 1.

Finally, the method 100 includes comparison of the fatigue damage based on the actual test data 412 with the fatigue damage based on the predicted test data 420 at a block 120. For example, FIG. 6 is a representative plot 600 of damage versus time for comparing the actual and predicted fatigue damages (block 120). As shown in FIG. 6, a set of actual damage data 602 is compared with a set of predicted damage data 604.

Because the method 100 may be performed in substantially real-time during a structural test, the actual damage data 602 may be rapidly compared with the predicted damage data 604 which may be useful for validation of the test data, and may provide an immediate indication of how variances in the applied actuator loads are affecting the severity of the test (i.e., undertesting or overtesting). In a presently preferred embodiment, the method 100 utilizes a spreadsheet program (e.g., Microsoft EXCEL) that enables test set parameters (FIG. 2) to be rapidly changed, and the results of such changes may be immediately determined and assessed by viewing the computation results (block 120). In some embodiments, various portions of the method 100 shown in FIG. 1 are performed simultaneously for all control points (sensors) on the test article. In one specific embodiment, for example, the crack initiation portion 110 of the method 100 is performed simultaneously for all control points.

Embodiments of methods and systems in accordance with the present invention may provide significant advantages over the prior art. In conventional structural testing, the massive quantities of data necessary to evaluate spectrum severity of applied to full-scale test article were collected and recorded during a structural test by data acquisition system, reformatted, and transferred to a separate computing system for analysis and interpretation by structural engineers. During the analysis interpretation, the structural engineers evaluate whether the test data were valid, and if so, would then calculate the spectrum severity. The structural engineers would analyze each control point independently, essentially repeating the same task several times. If the test data were not valid, appropriate corrections were made and the structural testing would be repeated, requiring considerable time and expense. However, methods and systems in accordance for the present invention enable analysis of the structural test data in real-time during a test. Based on the comparison at block 120, the test engineers may make appropriate adjustments to the applied actuator loads or to other variables involved in the test, or may be assured that the test setup is providing valid and accurate test results. Embodiments of the present invention provide the capability to calculate and compare crack initiation damage real-time, enabling test personnel to evaluate the effects of applied test load variances and make necessary adjustments while conducting a test. Thus, methods and systems in accordance with the present invention are efficient, inexpensive, and robust, and advantageously reduce the time and expense associated with providing accurate structural fatigue test results.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A method of analyzing structural test data, comprising:

applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data;

performing a second fatigue damage computation based on the predicted test data; and providing an indication of the first and second fatigue damage computations to enable a comparison of the first and second fatigue damage computations.

2. The method of claim, 1 wherein at least one of performing a first fatigue damage computation and performing a second fatigue damage computation includes performing a crack initiation computation.

3. The method of claim 1, wherein performing a first fatigue damage computation comprises performing a crack initiation computation.

4. A method of analyzing structural test data, comprising:
applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data, including performing a crack initiation computation, wherein performing a crack initiation computation includes calculating notch stress and strain based on the raw test data indicative of the applied load and an elastic $K_T$;

performing a second fatigue damage computation based on the predicted test data; and providing an indication of the first and second fatigue damage computations to enable a comparison of the first and second fatigue damage computations.

5. The method of claim 4, wherein calculating notch stress and strain includes calculating notch stress and strain based on a nominally elastic Neuber's Equation.

6. The method of claim 4, wherein performing a crack initiation computation includes correcting a calculated notch strain for load cycle stress ratio effects.

7. The method of claim 6, wherein correcting a calculated notch strain for load cycle stress ratio effects includes correcting a calculated notch strain for load cycle stress ratio effects using a Smith, Watson, and Topper equivalent stress equation.

8. A method of analyzing structural test data, comprising:
applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data, including performing a crack initiation computation, wherein performing a crack initiation computation includes calculating at least one of a damage and a failure criteria;

performing a second fatigue damage computation based on the predicted test data; and providing an indication of the first and second fatigue damage computations to enable a comparison of the first and second fatigue damage computations.

9. The method of claim 8, wherein calculating at least one of a damage and a failure criteria includes performing a summation of the calculated damage associated with continued load cycling using a Palmugren and Miner's Rule.

10. The method of claim 8, wherein calculating at least one of a damage and a failure criteria includes assuming a crack initiation occurs when a total damage is greater than or equal to 1.0.

11. A method of analyzing structural test data, comprising:
applying a sequence, of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data;

performing a second fatigue damage computation based on the predicted test data; and providing an indication of the first and second fatigue damage computations to enable a comparison of the, first and second fatigue damage computations, wherein the comparison of the first and second fatigue damage computations includes the comparison of a first damage summation associated with a first continued load cycling with a second damage summation associated with a second continued load cycling.

12. A method of analyzing structural test data, comprising:
applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data;

performing a second fatigue damage computation based on the predicted test data; and providing an indication of the first and second fatigue damage computations to enable a comparison of the first and second fatigue damage computations, wherein performing a first fatigue damage computation includes performing a first fatigue damage computation simultaneously with performing a second fatigue damage computation.

13. The method of claim 12, wherein performing a first fatigue damage computation simultaneously with performing a second fatigue damage computation includes simultaneously performing the first and second fatigue damage computations using a spreadsheet program.

14. A method of analyzing structural test data, comprising:

applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data;

performing a second fatigue damage computation based on the predicted test data; and providing an indication of the first and second fatigue damage computations to enable a comparison of the first and second fatigue damage computations, wherein at least one of performing a first fatigue damage computation and performing a second fatigue damage computation includes performing a respective damage computation using a spreadsheet program.

15. The method of claim 14, wherein comparing the first and second fatigue damage computations includes comparing the first and second fatigue damage computations simultaneously with at least one of performing a first fatigue damage computation and performing a second fatigue damage computation using a spreadsheet program.

16. The method of claim 14, wherein performing a cycle counting operation to pair peak and valley loads includes performing a rainflow cycle counting operation to pair peak and valley loads.

17. A method of analyzing structural test data, comprising:

applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data;

performing a second fatigue damage computation based on the predicted test data; and providing an indication of the first and second fatigue damage computations to enable a comparison of the first and second fatigue damage computations, wherein the following portions are performed simultaneously:

performing a filter to eliminate invalid data from the applied and predicted loads;

performing a cycle counting operation to pair peak and valley loads;

performing a first fatigue damage computation based on the raw test data; and performing a second fatigue damage computation on the predicted test data.

18. The method of claim 17, wherein the following portions are performed simultaneously:

applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data; and performing a second fatigue damage computation based on the predicted test data.

19. A computer program product for analyzing structural test data, comprising:

a first portion configured to receive raw test data indicative of applied loads from at least one sensor operatively associated with a test article;

a second portion configured to receive predicted test data indicative of predicted loads on the test article;

a third portion configured to perform a filter to remove invalid test data from the applied test data and the predicted test data;

a fourth portion configured to perform a cycle counting operation on the applied test data and the predicted test data;

a fifth portion configured to perform a first fatigue damage computation based on the raw test data;

a sixth portion configured to perform a second fatigue damage computation based on the predicted test data; and a seventh portion configured to provide an indication of the first and second fatigue damage computations to enable a comparison of the first and second fatigue damage computations.

20. The computer program product of claim 19, wherein at least one of the fifth portion and the sixth portion is further configured to perform a crack initiation computation.

21. The computer program product of claim 19, wherein the fifth portion is further configured to perform a crack initiation computation.

22. The computer program product of claim 19, wherein the fifth portion is further configured to calculate notch stress and strain based on the raw test data indicative of the applied load and an elastic $K_T$.

23. The computer program product of claim 22, wherein the fifth portion is further configured to calculate notch stress and strain based on a nominally elastic Neuber's Equation.

24. The computer program product of claim 22, wherein the fifth portion is further configured to correct a calculated notch strain for load cycle stress ratio effects.

25. The computer program product of claim 24, wherein the fifth portion is further configured to correct a calculated notch strain for load cycle stress ratio effects using a Smith, Watson, and Topper equivalent stress equation.

26. The computer program product of claim 21, wherein the fifth portion is further configured to perform a crack initiation computation including calculating at least one of a damage and a failure criteria.

27. The computer program product of claim 26, wherein the fifth portion is further configured to perform a summation of the calculated damage associated with continued load cycling using a Palmgren and Miner's Rule.

28. The computer program product of claim 26, wherein the fifth portion is further configured to assume a crack initiation occurs when a total damage is greater than or equal to 1.0.

29. The computer program product of claim 19, wherein the seventh portion is further configured to compare a first damage summation associated with a first continued load cycling with a second damage summation associated with a second continued load cycling.

30. The computer program product of claim 19, wherein the fifth portion is further configured to performing a first fatigue damage computation simultaneously with the performance of the second fatigue damage computation.

31. The computer program product of claim 30, wherein at least one of the fifth portion and the sixth portion is further configured to simultaneously performing the first and second fatigue damage computations using a spreadsheet program, respectively.

32. The computer program product of claim 30, wherein at least one of the fifth portion and the sixth portion is further configured to perform a respective damage computation using a spreadsheet program.

33. The computer program product of claim 19 wherein the seventh portion is further configured to compare the first and second fatigue damage computations simultaneously with at least one of performing a first fatigue damage computation by the fifth portion and performing a second fatigue damage computation by the sixth portion using a spreadsheet program.

34. The computer program product of claim 19, wherein the fourth portion is further configured to perform a rainflow cycle counting operation to pair peak and valley loads.

35. The computer program product of claim 19, wherein the third, fourth, fifth, and sixth portions are configured to perform simultaneously.

36. The computer program product of claim 19, wherein the first, second, third, fourth, fifth, sixth and seventh portions are configured to perform simultaneously.

37. A method of performing a structural test, comprising:
operatively coupling at least one sensor to a test article;
applying a sequence of loads to the test article;
receiving raw test data indicative of the applied loads from the at least one sensor;
analyzing the raw test data, including:
receiving predicted test data indicative of a predicted load on the test article;
performing a filter operation to remove invalid data including spikes and dropouts;
performing a cycle counting operation to pair peak and valley loads in the actual and predicted test data
performing a first fatigue damage computation based on the raw test data;
performing a second fatigue damage computation based on the predicted test data; and
providing an indication of the first and second fatigue damage computations to enable a comparison of the first and second fatigue damage computations.

38. The method of claim 37, wherein at least one of performing a first fatigue damage computation and performing a second fatigue damage computation includes performing a crack initiation computation.

39. The method of claim 38, wherein performing a crack initiation computation includes calculating notch stress and strain based on the raw test data indicative of the applied load and an elastic $K_T$.

40. The method of claim 38, wherein performing a crack initiation computation includes correcting a calculated notch strain for load cycle stress ratio effects.

41. The method of claim 38, wherein performing a crack initiation computation includes calculating at least one of a damage and a failure criteria.

42. The method of claim 37, wherein performing a first fatigue damage computation includes performing a first fatigue damage computation simultaneously with performing a second fatigue damage computation.

43. The method of claim 37, wherein performing a first fatigue damage computation simultaneously with performing a second fatigue damage computation includes simultaneously performing the first and second fatigue damage computations using a spreadsheet program.

44. The method of claim 37, wherein providing an indication of the first and second fatigue damage computations includes providing an indication of the first and second fatigue damage computations simultaneously with at least one of performing a first fatigue damage computation and performing a second fatigue damage computation using a spreadsheet program.

45. The method of claim 37, wherein performing a cycle counting operation to pair peak and valley loads includes performing a rainflow cycle counting operation to pair peak and valley loads.

46. The method of claim 37, wherein the following portions are performed simultaneously:
performing a filter to eliminate invalid data from the applied and predicted loads;
performing a cycle counting operation to pair peak and valley loads;
performing a first fatigue damage computation based on the raw test data; and
performing a second fatigue damage computation based on the predicted test data.

47. The method of claim 37, wherein the following portions are performed simultaneously:
applying a sequence of loads to a test article;
receiving raw test data indicative of the applied loads from at least one sensor operatively associated with the test article;
receiving predicted test data indicative of a predicted loads on the test article;
performing a filter to eliminate invalid data from the applied and predicted loads;
performing a cycle counting operation to pair peak and valley loads;
performing a first fatigue damage computation based on the raw test data; and
performing a second fatigue damage computation based on the predicted test data.

48. A method of analyzing structural test data, comprising:
applying a sequence of loads to a test article;
receiving raw test data indicative of the applied loads from at least one sensor operatively associated with the test article;
receiving predicted test data indicative of a predicted loads on the test article;
performing a filter operation to remove invalid loads from the raw and predicted test data;
performing a cycle counting operation to pair peak and valley loads in the raw and predicted data;
performing a first fatigue damage computation based on the raw test data;

performing a second fatigue damage computation based on the predicted test data; and providing an indication of the first and second fatigue damage computations to enable a comparison of the first and second fatigue damage computations, wherein at least one of the performing of the first and second fatigue damage computations includes performing a crack initiation computation including calculating notch stress and strain based on the raw test data indicative of the applied load and an elastic $K_T$;

correcting a calculated notch strain for load cycle stress ratio effects; and calculating at least one of a damage and a failure criteria.

49. The method of claim 48, wherein calculating notch stress and strain includes calculating notch strain for load cycle stress ratio effects using a Smith, Watson, and Topper equivalent stress equation.

50. The method of claim 48, wherein correcting a calculated notch strain for load cycle stress ratio effects includes correcting a calculated notch strain for load cycle stress ratio effects using a Smith, Watson, and Topper equivalent stress equation.

51. The method of claim 48, wherein calculating at least one of a damage and a failure criteria includes performing a summation of the calculated damage associated with continued load cycling using a Palmgren and Miner's Rule.

52. The method of claim 48, wherein calculating at least one of a damage and a failure criteria includes assuming a crack initiation occurs when a total damage is greater than or equal to 1.0.

53. The method of claim 48, wherein providing an indication of the first and second fatigue damage computations includes providing an indication of a first damage summation associated with a first continued load cycling with a second damage summation associated with a second continued load cycling.

54. The method of claim 48, wherein performing a first fatigue damage computation includes performing a first fatigue damage computation simultaneously with performing a second fatigue damage computation.

55. The method of claim 48, wherein performing a first fatigue damage computation simultaneously with performing a second fatigue damage computation includes simultaneously performing the first and second fatigue damage computations using a spreadsheet program.

56. The method of claim 48, wherein at least one of performing a first fatigue damage computation and performing a second fatigue damage computation includes performing a respective damage computation using a spreadsheet program.

57. The method of claim 48, wherein providing an indication of the first and second fatigue damage computations includes providing an indication of the first and second fatigue damage computations simultaneously with at least one of performing a first fatigue damage computation and performing a second fatigue damage computation using a spreadsheet program.

58. The method of claim 48, wherein performing a cycle counting operation to pair peak and valley loads includes performing a rainflow cycle counting operation to pair peak and valley loads.

59. The method of claim 48, wherein the following portions are performed simultaneously:

performing a filter to eliminate invalid data from the applied and predicted loads;

performing a cycle counting operation to pair peak and valley loads;

performing a first fatigue damage computation based on the raw test data; and performing a second fatigue damage computation based on the predicted test data.

60. The method of claim 48, wherein the following portions are performed simultaneously:

applying a sequence of loads to a test article;

receiving raw test data indicative of the applied loads from at least one sensor operatively associated with the test article;

receiving predicted test data indicative of a predicted loads on the test article;

performing a filter to eliminate invalid data from the applied and predicted loads;

performing a cycle counting operation to pair peak and valley loads;

performing a first fatigue damage computation based on the raw test data; and performing a second fatigue damage computation based on the predicted test data.

* * * * *